United States Patent
Yang

(10) Patent No.: US 10,940,335 B2
(45) Date of Patent: Mar. 9, 2021

(54) ULTRASOUND STIMULATION HELMET

(71) Applicant: National Yang-Ming University, Taipei (TW)

(72) Inventor: Feng-Yi Yang, Taipei (TW)

(73) Assignee: National Yang-Ming University, Taipei (TW)

( * ) Notice: Subject to any disclaimer, the term of this patent is extended or adjusted under 35 U.S.C. 154(b) by 405 days.

(21) Appl. No.: 15/767,516

(22) PCT Filed: Oct. 15, 2015

(86) PCT No.: PCT/CN2015/092005
§ 371 (c)(1),
(2) Date: Apr. 11, 2018

(87) PCT Pub. No.: WO2017/063172
PCT Pub. Date: Apr. 20, 2017

(65) Prior Publication Data
US 2018/0304101 A1    Oct. 25, 2018

(51) Int. Cl.
*A61N 7/00* (2006.01)
*A61B 17/225* (2006.01)
(Continued)

(52) U.S. Cl.
CPC .............. *A61N 7/00* (2013.01); *A61B 17/22* (2013.01); *A61B 17/225* (2013.01); *A61H 23/00* (2013.01);
(Continued)

(58) Field of Classification Search
CPC .............. A61N 7/00; A61N 2007/0026; A61N 2007/0073; A61N 2007/0078; A61B 17/225; A61B 17/22; A61H 23/00
See application file for complete search history.

(56) References Cited

U.S. PATENT DOCUMENTS

2012/0289869 A1* 11/2012 Tyler .................. A61B 5/04008
601/2

FOREIGN PATENT DOCUMENTS

| CN | 2683174 Y | 3/2005 |
| CN | 1689662 A | 11/2005 |

(Continued)

OTHER PUBLICATIONS

Wei-Ting Lin, et al., Protective effects of low-intensity pulsed ultrasound on aluminum-induced cerebral damage in Alzheimer's disease rat model, Scientific Reports, Apr. 15, 2015, pp. 1-7.

*Primary Examiner* — Joel Lamprecht
(74) *Attorney, Agent, or Firm* — Muncy, Geissler, Olds and Lowe, P.C.

(57) ABSTRACT

An ultrasound stimulation helmet (100) configured to regulate an endogenous neurotrophic factor in a brain or expression of proteins related to a neurodegenerative disease comprises: a main body (1) having a forehead perimeter adjustment knob (12), a back head perimeter adjustment knob (13), a fastening support frame (14), and multiple position adjustment knobs (15); and multiple ultrasound probes (2) detachably mounted on the main body (1), wherein the ultrasound probe (2) has a frequency adjustment button and an intensity adjustment button to respectively control an output frequency and output intensity of the ultrasound probe (2), and other ultrasound parameters and an angle of the ultrasound probe (2) itself are adjustable as well. The fastening support frame (14) can be used to adjust the length of the main body (1) according to the size of a head of a patient, and the ultrasound probes (2) are connected to the position adjustment knobs (15) to enable the ultrasound probes (2) to move upward, downward, or toward the left or right with respect to the head of the patient.

9 Claims, 19 Drawing Sheets

(51) Int. Cl.
    *A61B 17/22*     (2006.01)
    *A61H 23/00*     (2006.01)

(52) U.S. Cl.
    CPC ......... *A61N 2007/0026* (2013.01); *A61N 2007/0073* (2013.01); *A61N 2007/0078* (2013.01)

(56) References Cited

FOREIGN PATENT DOCUMENTS

| | | | |
|---|---|---|---|
| CN | 102791332 | A | 11/2012 |
| CN | 203494074 | U | 3/2014 |
| CN | 104548390 | A | 4/2015 |
| CN | 104857641 | A | 8/2015 |

* cited by examiner

ULTRASOUND STIMULATION HELMET

CROSS-REFERENCE TO RELATED APPLICATIONS

This is a National Phase Application filed under 35 U.S.C. 371 as a national stage of PCT/CN2015/092005 filed Oct. 15, 2015, the content of which is hereby incorporated by reference in its entirety.

FIELD OF THE INVENTION

The present invention provides a novel ultrasound stimulation helmet. The ultrasound stimulation helmet could regulate the expression of brain endogenous neurotrophic factors and neurodegenerative disease-related protein to prevent and treat the neurodegenerative brain disease.

BACKGROUND OF THE INVENTION

The neurodegenerative diseases of the brain include Alzheimer's disease, depression or Parkinson's disease etc. Current main treatments for these neurodegenerative diseases include implant the drugs, the nerve growth factors or the stem cells to induce the regeneration of the nerve cells of the brain. However, these invasive methods require the opening of the blood-brain barrier (BBB), the damage of the blood-brain barrier or the brain tissue is concerned.

In addition, the current therapeutic drugs are only used to control or slow down the symptoms of neurodegenerative diseases. They can't completely cure the neurodegenerative diseases. Moreover, long-term administration of the drugs will cause side effects such as nausea, vomiting, diarrhea, drowsiness, or hallucinations.

SUMMARY OF THE INVENTION

Accordingly, the present invention provides an ultrasound stimulation helmet for regulating the expression of a brain endogenous neurotrophic factor and a neurodegenerative disease-related protein. The helmet comprises a main body, which is wearable on a person's head. The main body comprising a front adjustment knob, a back adjustment knob, a fastening support frame, and a plurality of position adjustment knobs. Furthermore, the helmet comprising a plurality of ultrasound probes detachably mounted on the main body for generating ultrasound waves. The ultrasound probes comprising a frequency adjustment knob and an intensity adjustment knob for controlling the frequency and the intensity of the ultrasound waves respectively, and other ultrasound wave parameters and the angle of the ultrasound probe can also be adjusted. The fastening support frame can adjust the length of the main body according to the size of the head of the patient, and the ultrasound probe is connected with the position adjustment knob of the main body so that the ultrasound probe can be moved up, down, left and right according to the patient's head.

In one embodiment of the present invention, the number of the ultrasound probes is 2-8. Preferably, the number of the ultrasound probes is 8.

In one embodiment of the present invention, the main body comprises a cable fixing portion for fixing the cables of the ultrasound probes.

In one embodiment of the present invention, the ultrasound probe comprises a power switch for turning on or off the ultrasound probes.

In one embodiment of the present invention, the frequency of ultrasound wave is between about 20K and about 10M Hz.

In one embodiment of the present invention, the intensity ($I_{SPTA}$) of ultrasound wave is between about 1 mW/cm$^2$ and about 10 W/cm$^2$.

The present invention also provides a method for regulating the expression of brain-derived neurotrophic factor or neurodegenerative disease-related protein, comprising: (1) Placing the above-mentioned ultrasound stimulation helmet on a subject's head; (2) Adjusting the parameters of the ultrasound probe of the ultrasound stimulation helmet to increase or decrease the expression level of endogenous neurotrophic factor or neurodegenerative disease-related protein in the brain of the subject.

In one embodiment of the present invention, the regulation of the expression of brain-derived neurotrophic factor or neurodegenerative disease-related protein includes increasing and decreasing.

In one embodiment of the present invention, the parameter of the adjusted ultrasound probe in the step (2) comprising an output intensity ($I_{SPTA}$), an output frequency, an action time or other parameters.

In one embodiment of the present invention, the output intensity is between about 1 mW/cm$^2$ and about 1 W/cm$^2$.

In one embodiment of the present invention, the output frequency is between about 20K and about 10M Hz.

In one embodiment of the present invention, the action time is between about 30 seconds and about 60 minutes.

In one embodiment of the present invention, the brain endogenous neurotrophic factor is selected from one or more of the group consisting of brain-derived neurotrophic factor (BDNF), glial cell-derived neurotrophic factor (GDNF), vascular endothelial growth factor (VEGF) and c-fos protein.

In one embodiment of the present invention, the neurodegenerative disease-related protein is selected from one or more of the group consisting of TrkB, β-amyloid and acetyl coenzyme A.

DETAILED DESCRIPTION OF THE INVENTION

The ultrasound stimulation helmet 100 of the present invention can be used for regulating the expression level of brain endogenous neurotrophic factor or neurodegenerative disease-related protein.

The "brain endogenous neurotrophic factor" of the present invention includes brain-derived neurotrophic factor (BDNF), glial cell-derived neurotrophic factor (GDNF), vascular endothelial growth factor (VEGF) or c-fos protein.

The "neurodegenerative disease-related protein" of the present invention includes TrkB, β-amyloid or acetyl coenzyme A.

As used herein, "regulating" includes increasing or decreasing the expression of brain endogenous neurotrophic factor or neurodegenerative disease-related protein.

Figure 1A:
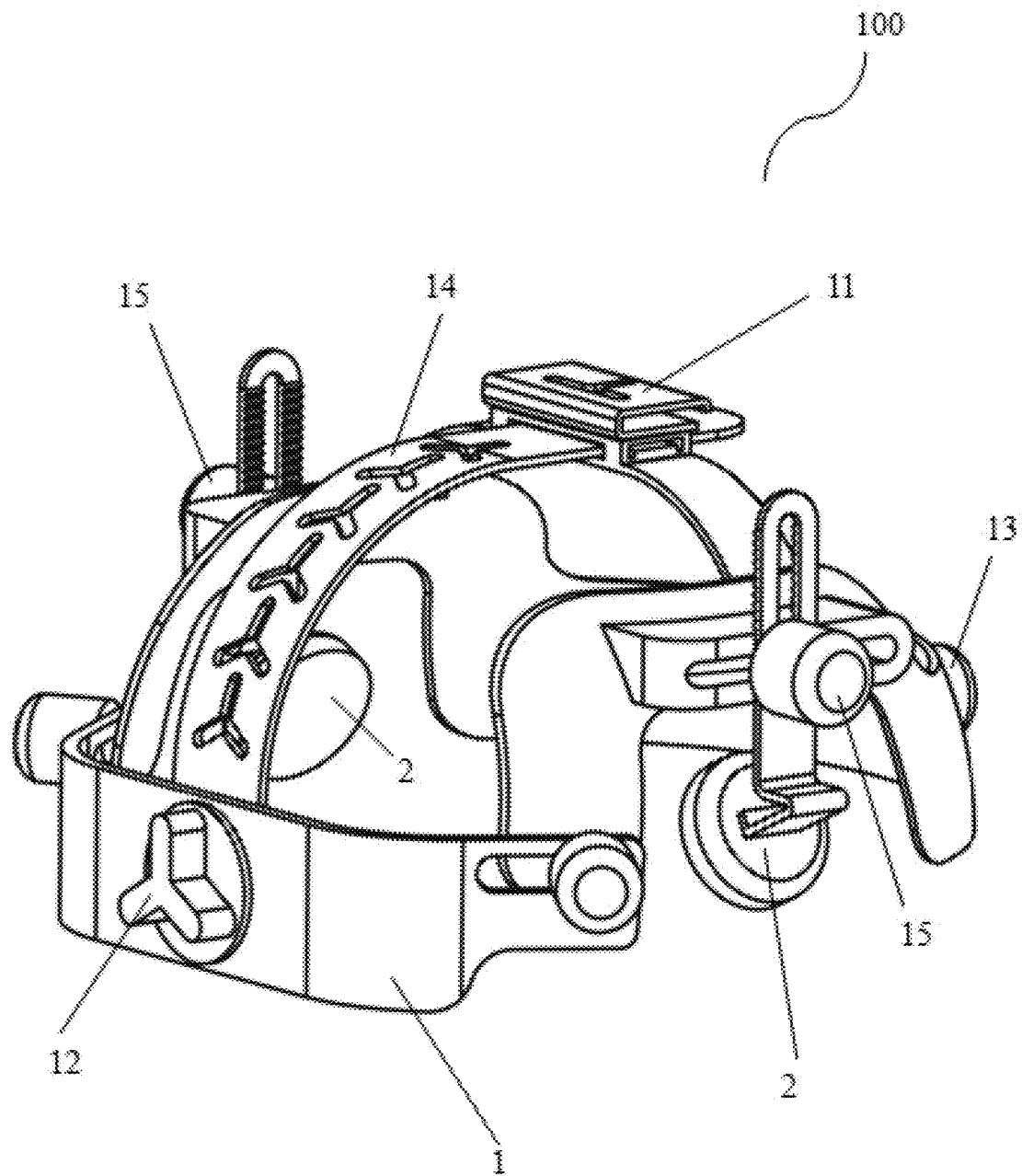
FIG. 1A is a schematic front view of the ultrasound stimulation helmet with two ultrasound probes of the present invention.
Figure 1B:
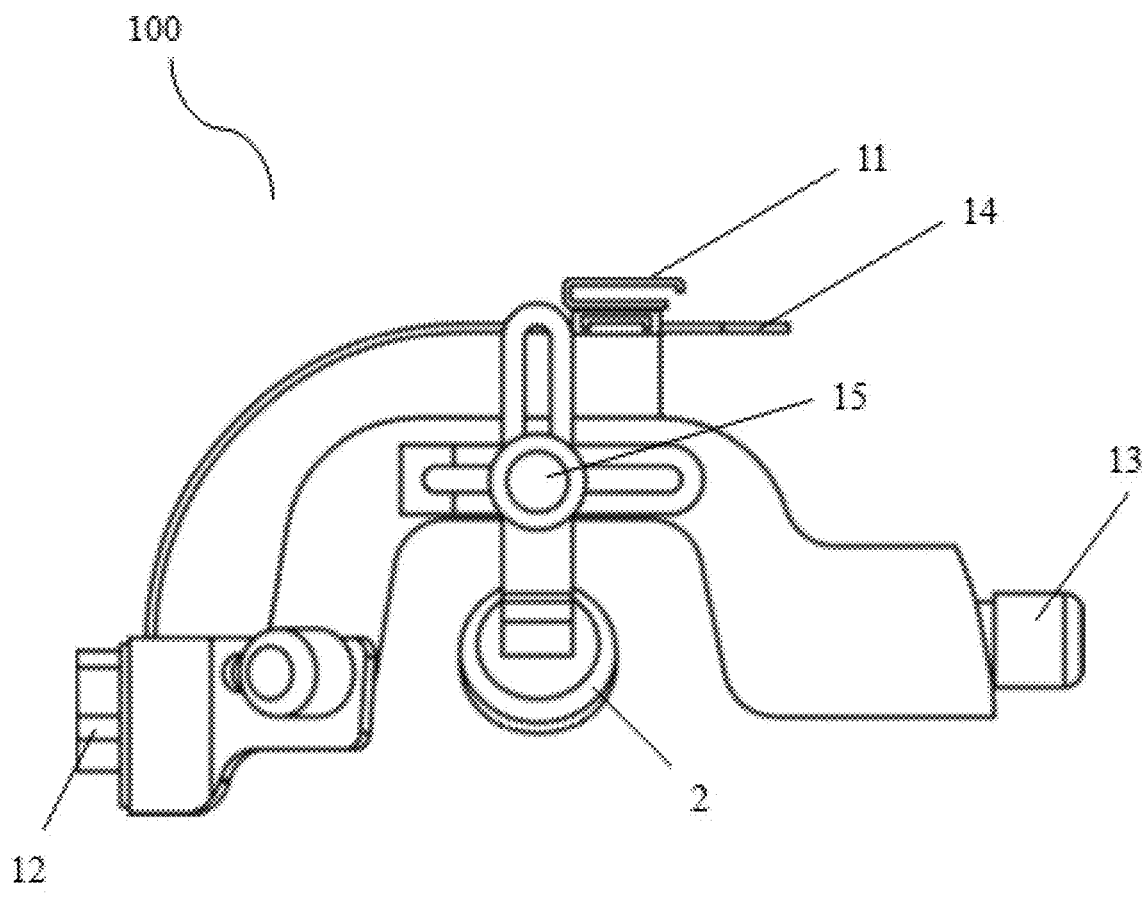
FIG. 1B is a schematic lateral view of the ultrasound stimulation helmet with two ultrasound probes of the present invention.
Figure 2:
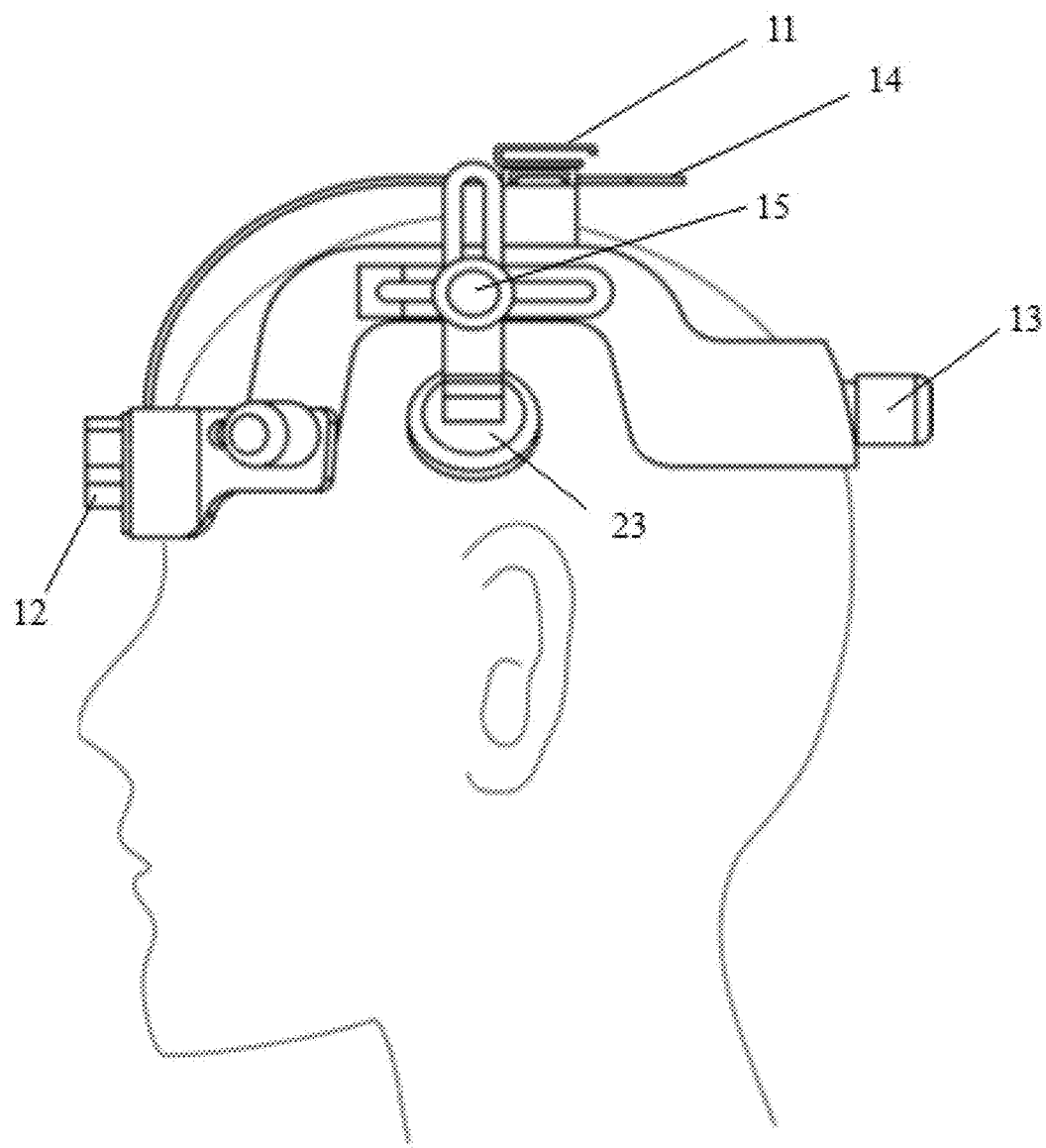
FIG. 2 is a schematic diagram of the ultrasound stimulation helmet of the present invention worn on the head of a subject.

As shown in FIGS. 1A and 1B, the ultrasound stimulation helmet 100 of the present invention includes a main body 1 that is wearable on a patient's head (as shown in FIG. 2) and a plurality of ultrasound probes 2 that are detachably mounted on the main body 1.

As shown in FIG. 1A and FIG. 1B, the main body 1 includes a cable fixing portion 11 for fixing the cable of the ultrasound probe 2, a front adjustment knob 12 is used to adjust according to the patient's head circumference; a back adjustment knob 13, is used to cooperated with the front adjustment knob 12 so that the ultrasound stimulation helmet 100 can be fixed to the patient's head through the design of the forehead support to prevent the ultrasound stimulation helmet 100 from sliding. The fastening support frame 14 can adjust the length of the main body 1 according to the patient's head; and a plurality of position adjustment knobs 15 are connected to the ultrasound probe 2, so that the ultrasound probe 2 can move up, down, left and right relative to the patient's head. In addition, the main body 1 is mainly made of plastic hardware and a metal bracket, and a cushion is used on the inner side of the main body 1 to reduce the friction between the ultrasound stimulation helmet 100 and the patient's head.

Figure 3A:
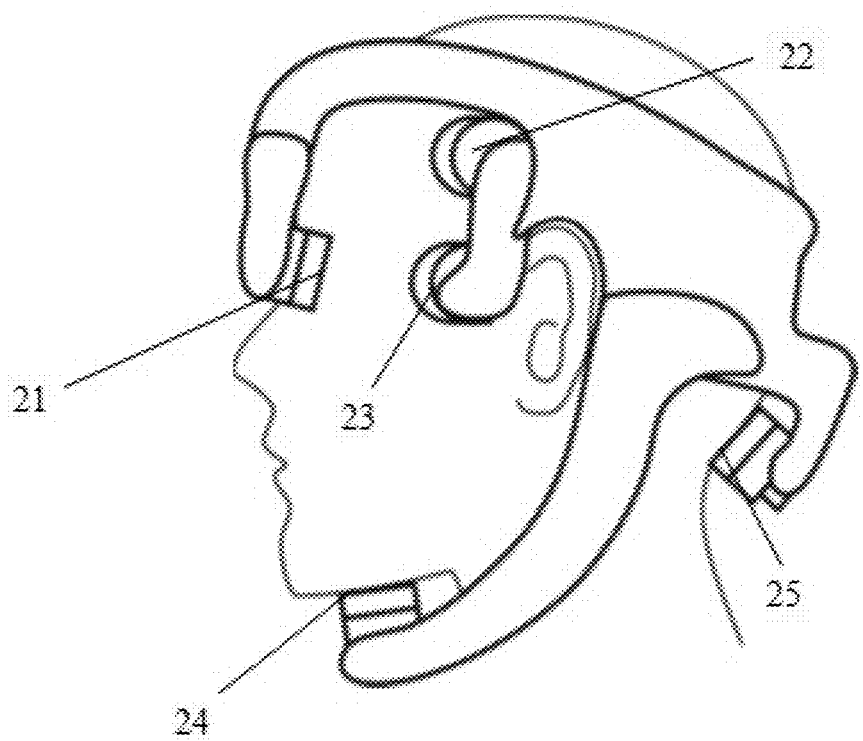
FIG. 3A is a schematic lateral view of the ultrasound stimulation helmet with eight ultrasound probes of the present invention from left position.
Figure 3B:
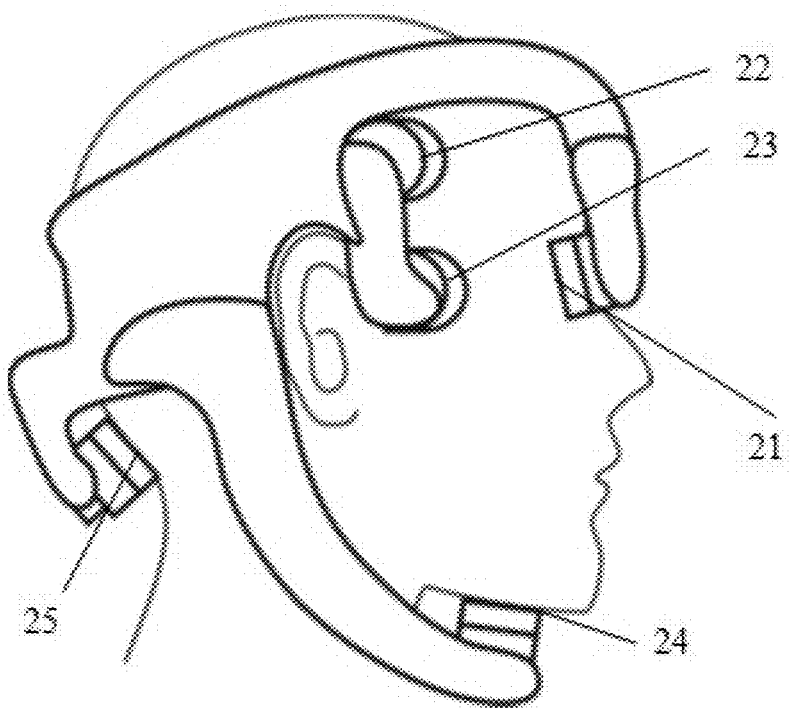
FIG. 3B is a schematic lateral view of the ultrasound stimulation helmet with eight ultrasound probes of the present invention from right position.

The ultrasound stimulation helmet 100 of the present invention may include 2-8 ultrasound probes 2 placed in a position as shown in FIGS. 3A and 3B, which is positioned relative to the patient's temporal trans-orbital 21, frontal-temporal cortex 22, temporal window 23, sub-mandibular 24, sub-occipital window 25. FIG. 1A and FIG. 1B only show two ultrasound probes 2, which are positioned relative to the patient's temporal window 23 (as shown in FIG. 2).

There is a built-in piezoelectric sheet (not shown in figures) in each ultrasound probes 2 for generating ultrasound waves, and each built-in piezoelectric sheet comprising a switch (not shown in figures), a frequency adjustment knob (not shown in figures), and an intensity adjustment knob (not shown in figures), wherein the switch can turn on or turn off the ultrasound probe 2 alone, so that the ultrasound stimulation helmet 100 of the present invention can apply ultrasound waves to the desired treatment position according to different patient's symptoms. In addition, the frequency adjustment button and the intensity adjustment button are used to control the output frequency and output intensity of the ultrasound probe 2 respectively, and other ultrasound parameters can be adjusted, and the ultrasound probe 2 itself can be adjusted to the desired application. Therefore, when the ultrasound probe 2 is placed at different positions, different output frequencies and output intensities may be used in combination so that the ultrasound stimulation helmet 100 of the present invention can increases the brain endogenous neurotrophic factor in certain part of the brain, and reduce the neurodegenerative disease-related protein in another part of the brain simultaneously.

The parameter of the ultrasound probe 2 is set to have a lower applied energy, wherein the output intensity ($I_{SPTA}$) is 1 mW/cm$^2$–1 W/cm$^2$ and the output frequency is 20K-10 MHz. Therefore, during the treatment, the ultrasound output from each ultrasound probe 2 would not increase or decrease the neurotrophic factor, calcium or TrkB level through the pathway, but increase or decrease the neurotrophic factor, calcium or TrkB level in the ultrasound treated area. In addition, the ultrasound probe 2 has the function of detecting and treating at the same time. When the detected neurotrophic factor, calcium or TrkB level is too much or little in the brain cells of the patient, the frequency, intensity and other functional parameters of the ultrasound probe 2 can be changed in real time to the treat patients.

Example 1. The Effect of Ultrasound Stimulation on the Endogenous Neurotrophic Factor in Brain In the experimental group, the left and right hippocampus of Sprague-Dawley (SD) male rat were treated with low-intensity pulsed ultrasound stimulation with an output frequency of 0.3-1.0 MHz and an output power ($I_{SPTA}$) of 10-720 mW/cm$^2$ for seven consecutive days. The time of application was 15 minutes. Seven days later, SD male mice were sacrificed. Then detect the expression levels of the BDNF, GDNF and VEGF biomarker in brain of SD male rats were observed by Western blotting. The results are shown in FIGS. 4A, 4B and 4C, wherein the control group was the right and left hippocampi of SD male mice without applying low intensity pulsed ultrasound stimulation.

Figure 4A:
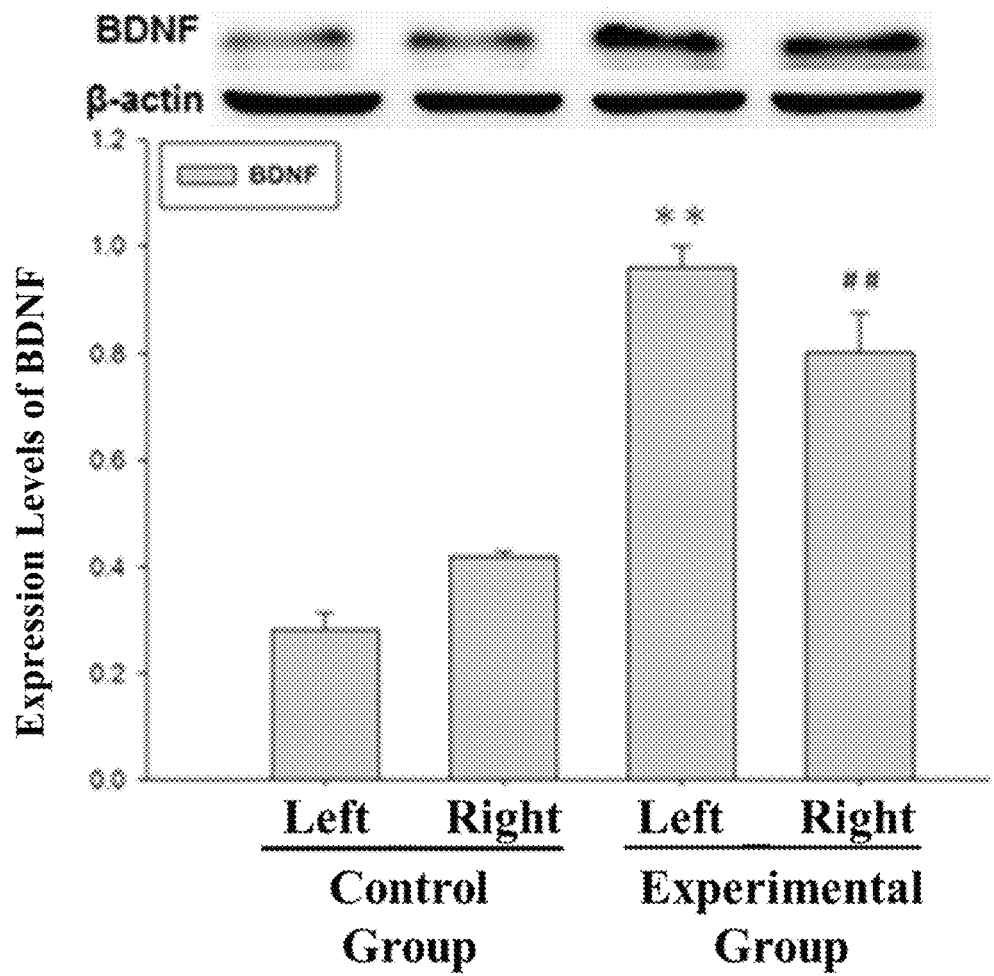
FIG. 4A shows the effect of ultrasound stimulation on BDNF expression in brain astrocytes.
Figure 4B:
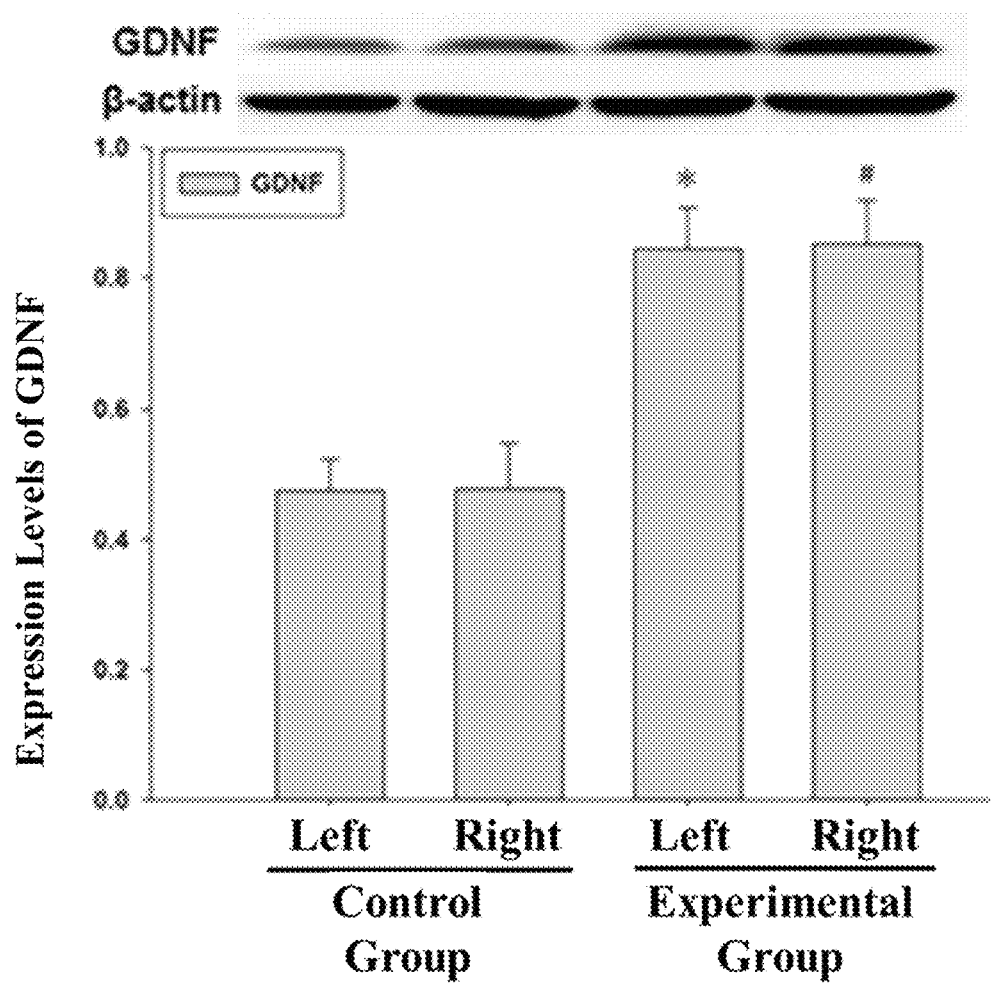
FIG. 4B shows the effect of ultrasound stimulation on GDNF expression in brain astrocytes.
Figure 4C:
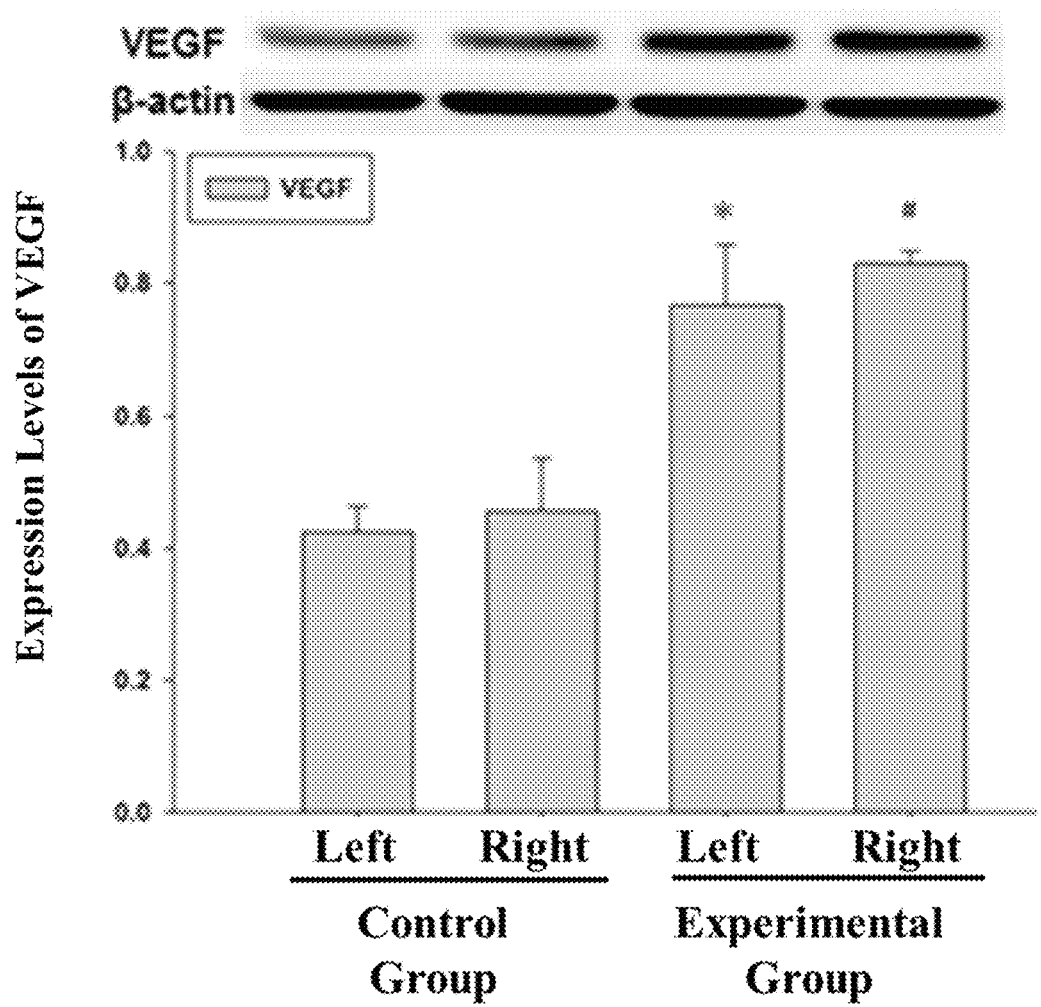
FIG. 4C shows the effect of ultrasound stimulation on VEGF expression in brain astrocytes.

From the experimental results, the neurons of SD male mice (experimental group) stimulated with low intensity pulsed ultrasound stimulation could activate the expression of brain neurotrophic factors, comparing to the control group, including BDNF (as shown in FIG. 4A), GDNF (as shown in FIG. 4B) and VEGF (as shown in FIG. 4C).

In addition, low intensity pulsed ultrasound stimulation with an output frequency of 0.3-1.0 MHz and an output power ($I_{SPTA}$) of 10-720 mW/cm$^2$ was applied to rat astrocytic cells (CTX TNA2) several times (experimental group).

Figure 5A:
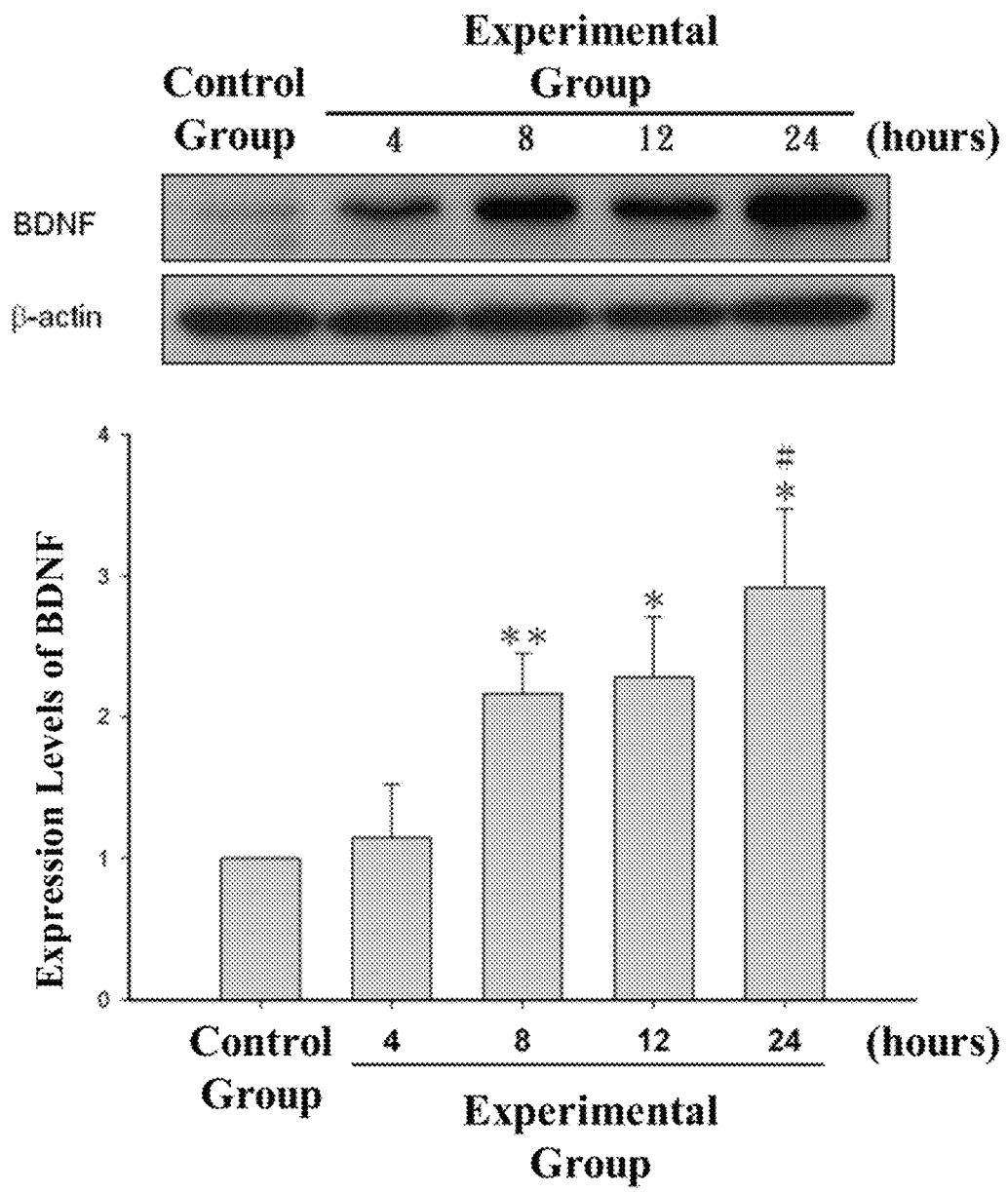
FIG. 5A shows the effect of ultrasound stimulation on brain BDNF expression at different times after stimulation of brain astrocytes.
Figure 5B:
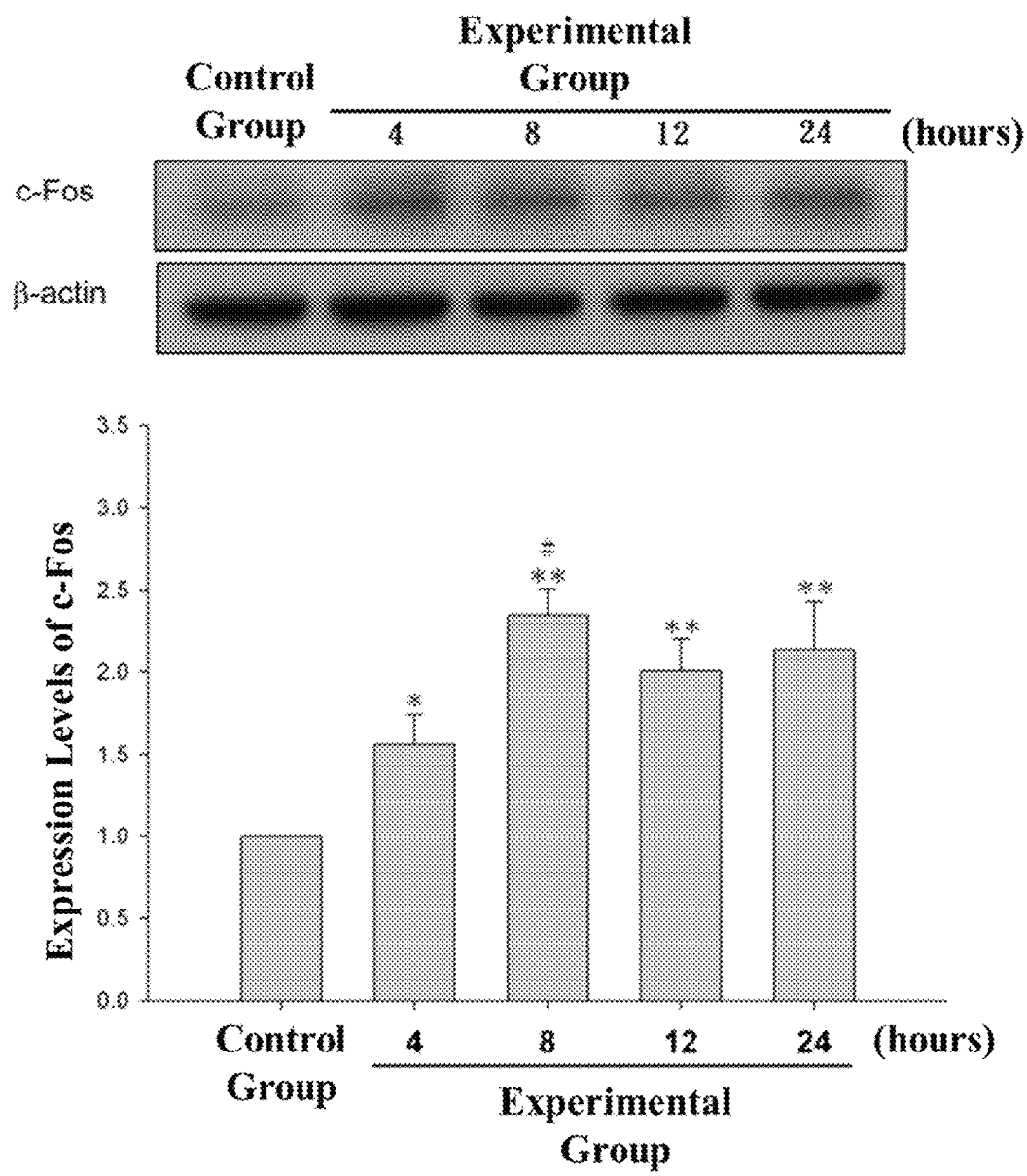
FIG. 5B shows the effect of ultrasound stimulation on brain c-Fos expression at different times after stimulation of brain astrocytes.

The time of application was 15 minutes. In the control group, the levels of protein expression of BDNF and c-Fos were measured by Western blotting before administration on 4, 8, 12 and 24 hours after application. In the experiment group, the results were shown in FIGS. 5A and 5B, BDNF (as shown in FIG. 5A) and c-Fos (as shown in FIG. 5B) all showed higher protein expression levels than the control group.

Example 2. The Effect of Ultrasound Stimulation on Intracellular Calcium Concentration Low-intensity pulsed ultrasound stimulation with an output frequency of 0.3-1.0 MHz and an output power ($I_{SPTA}$) of 10-720 mW/cm$^2$ was applied to rat brain astrocyte cells (CTX TNA2) several times (in the experimental group). The time of application was 5 minutes. The intracellular calcium concentration was measured by Western blotting at 0, 30, 60 and 120 seconds after the administration (in the control group) and before administration.

Figure 6:
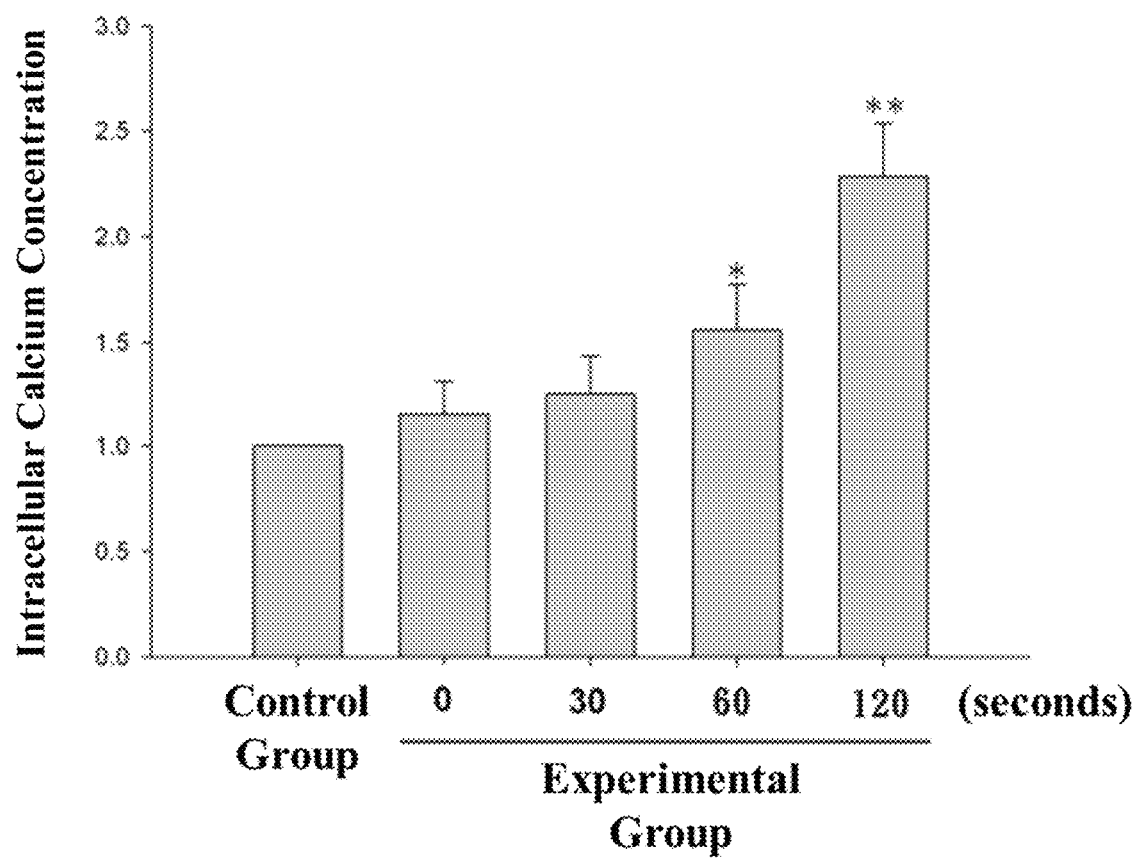
FIG. 6 shows the effect of ultrasound stimulation on intracellular calcium concentration in brain cells.

The results were shown in FIG. 6. Compared to the control group, the intracellular calcium concentration in the experimental group increased according to the increase of the ultrasound stimulation application time.

Example 3. The Effect of Ultrasound Stimulation on TrkB phosphorylation in the Cell Low-intensity pulsed ultrasound with an output frequency of 0.3-1.0 MHz and an output power ($I_{SPTA}$) of 10-720 mW/cm$^2$ was applied to rat brain astrocyte cells (CTX TNA2) several times (in the experimental group). The time of application was 5 minutes. The intracellular calcium concentration was measured by Western blotting at 0.5, 1, 2, and 4 hours after the administration (in the control group) and before administration.

Figure 7:
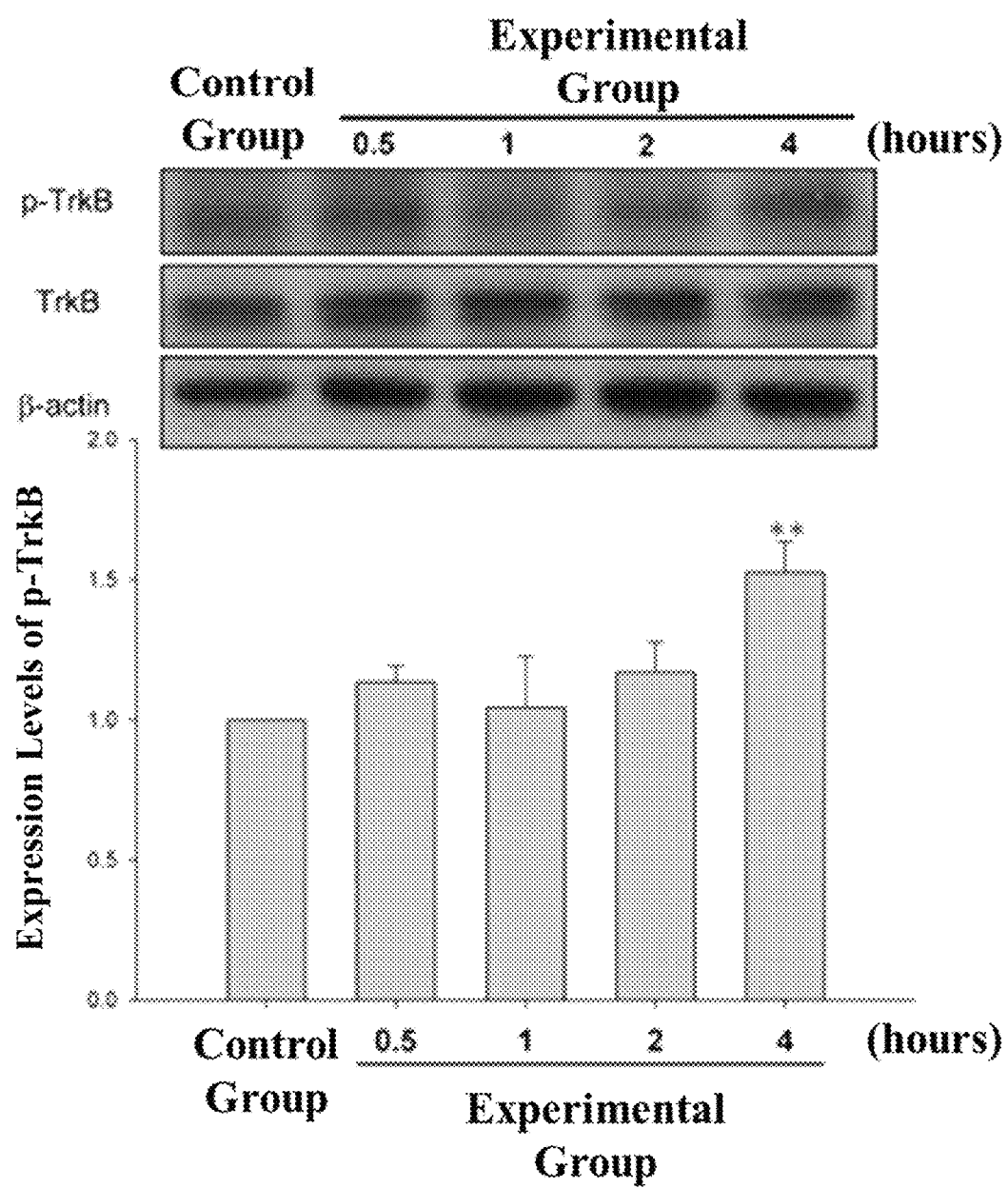
FIG. 7 shows the effect of ultrasound stimulation on TrkB phosphorylation in brain cells.

The results were shown in FIG. 7, the level of intracellular phosphorylated TrkB in the experimental group was higher than the control group, and level of phosphorylated TrkB (p-TrkB) at 4 hours after ultrasound stimulation was the highest.

Example 4. Effect of Ultrasound Stimulation on Neurodegenerative Disease-Protein Expression The SD male rats were divided into 4 groups: control group, ultrasound group, aluminum chloride group and experimental group, wherein the control group was not applied with low-intensity pulsed ultrasound and fed with water; ultrasound group was applied with output frequency of 0.3-1.0 MHz low intensity pulsed ultrasound stimulation at and output power ($I_{SPTA}$) of 10-720 mW/cm$^2$ continuously for 49 days; the aluminum chloride group did not have any treatment on day 0-7, and then on day 8-49 100 mg/kg aluminum chloride was continuously fed in the this group. The experimental group was also administered with continuous low-intensity pulsed ultrasound stimulation at the output frequency of 0.3-1.0 MHz and output power ($I_{SPTA}$) of 10-720 mW/cm$^2$ for 49 days, and fed 100 mg/kg aluminum chloride on day 8-49. All groups of SD male rat were sacrificed on the 49th day after feeding or administration, and Western blotting was used to measure the β-amyloid in the cortex and hippocampus and acetyl coenzyme A in the forebrain.

Figure 8A:
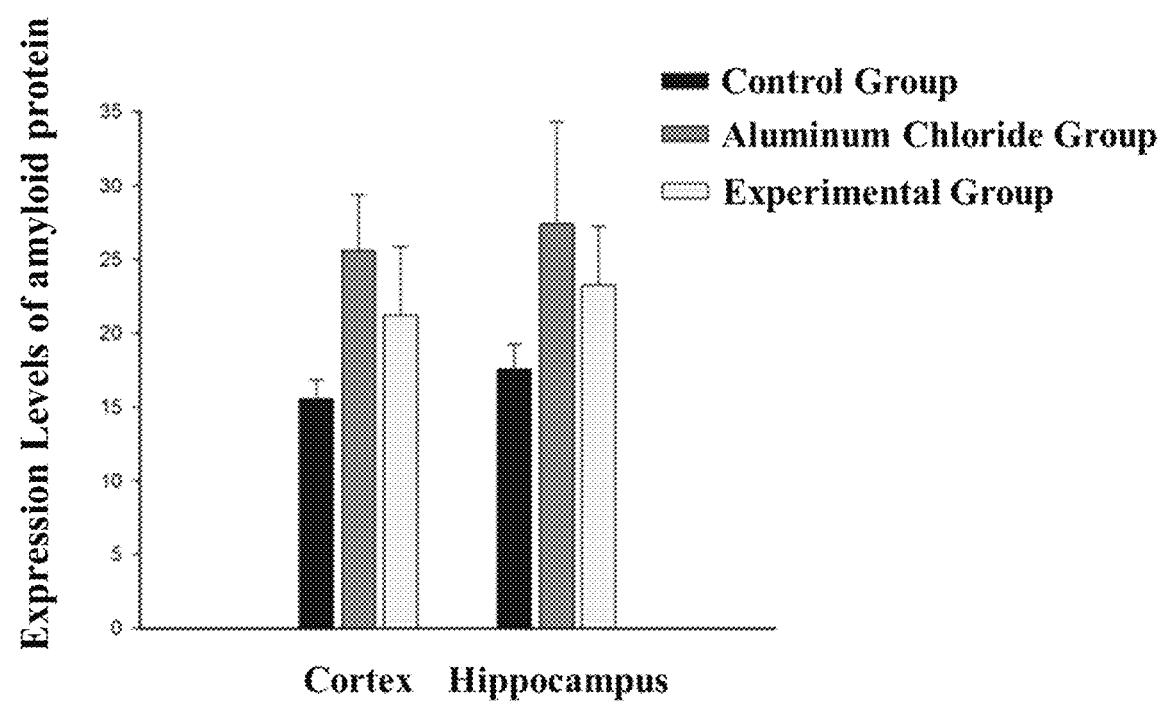
FIG. 8A shows the effect of ultrasound stimulation on beta-amyloid expression.

As shown in FIG. 8A, the level of amyloid protein (Aβ1-42) in SD male rats of the aluminum chloride group is higher than the control group. In the experimental group, due to the application of low-intensity pulsed ultrasound stimulation, the expression of amyloid protein (Aβ1-42) decreased significantly.

Figure 8B:
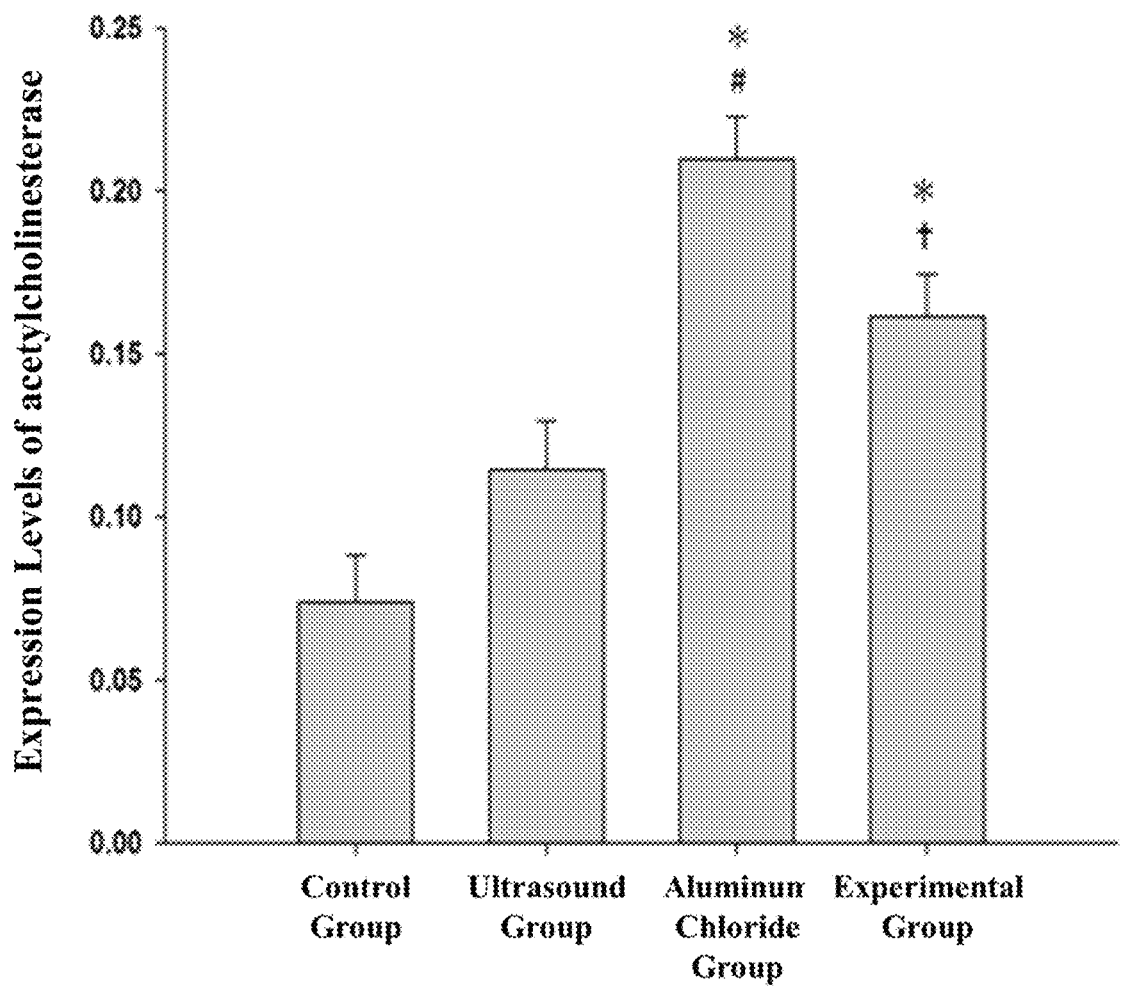
FIG. 8B shows the effect of ultrasound stimulation on acetyl coenzyme A expression.

In addition, as shown in FIG. 8B, acetylcholinesterase activity in the SD male rats of aluminum chloride group increased significantly (0.07±0.01 to 0.21±0.01; p<0.05) compared with the control group. In the experiment, the acetylcholinesterase activity in the forebrain had significantly decreased (0.21±0.01 to 0.16±0.01; p<0.05) in SD male rat due to low-intensity pulsed ultrasound stimulation. Based on the above results, low-intensity pulsed ultrasound stimulation can inhibit the expression of proteins associated with neurodegenerative diseases.

Example 5. Animal Behavior Test

The SD male rats were divided into 4 groups: control group, ultrasound group, vascular dementia group and experimental group. The difference between the control group and the vascular dementia group was, the bilateral carotid arteries did not be blocked after operation in the control group, whereas the bilateral carotid arteries permanently obstructed during the operation in the vascular dementia group. All the SD rats in the ultrasound group and in the experimental group were administered with ultrasound stimulation for fourteen days continuously after the fourteenth day of waiting period, wherein the ultrasound group did not make any treatment before the waiting period, while the experimental group received bilateral carotid artery occlusion.

Figure 9A:
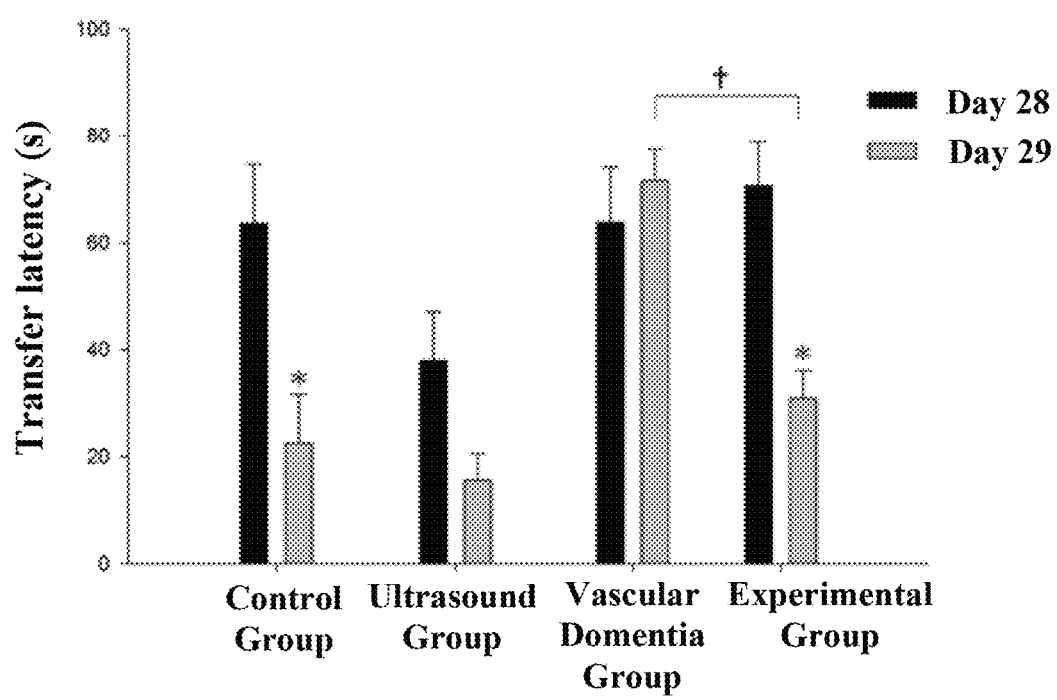
FIG. 9A shows the results of transfer latency of mice under different conditions.

On day 28 and day 29, SD male rats of four groups were placed in elevated plus maze test respectively, and the transfer latency was measured respectively. The results are shown in FIG. 9A. The transmission delay time of SD male rat decreased significantly on the 29th day in the control group and the ultrasound group. On the contrary, there was no significant difference in the transmission delay time between the 28th day and the 29th day of SD male mice in the vascular dementia group and in the experimental group, the transmission delay time of SD male mice stimulated by vascular dementia with low-intensity pulsed ultrasound was significantly shorter than that of the 28th day on the 29th day.

Figure 9B:
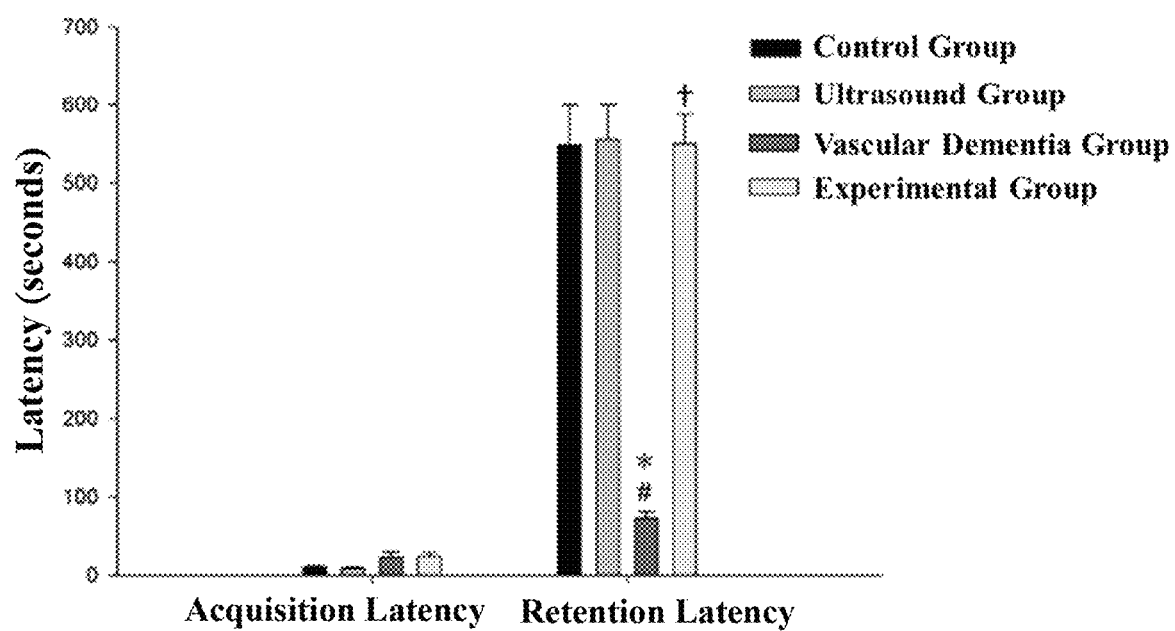
FIG. 9B shows the results of acquisition latency and retention latency of mice under different conditions.

In addition, four groups of SD male rats were subjected to Passive Avoidance Test. As shown in FIG. 9B, there was no significant difference in Acquisition Latency among the four groups of SD male rats. SD male rats in vascular dementia had significantly lower retention latency (Retention Latency); however, SD rats (i.e. experimental group) stimulated with low-intensity pulsed ultrasound showed a significant recovery of retention latency (Retention Latency) to the same with the control group and ultrasound group.

Figure 10:
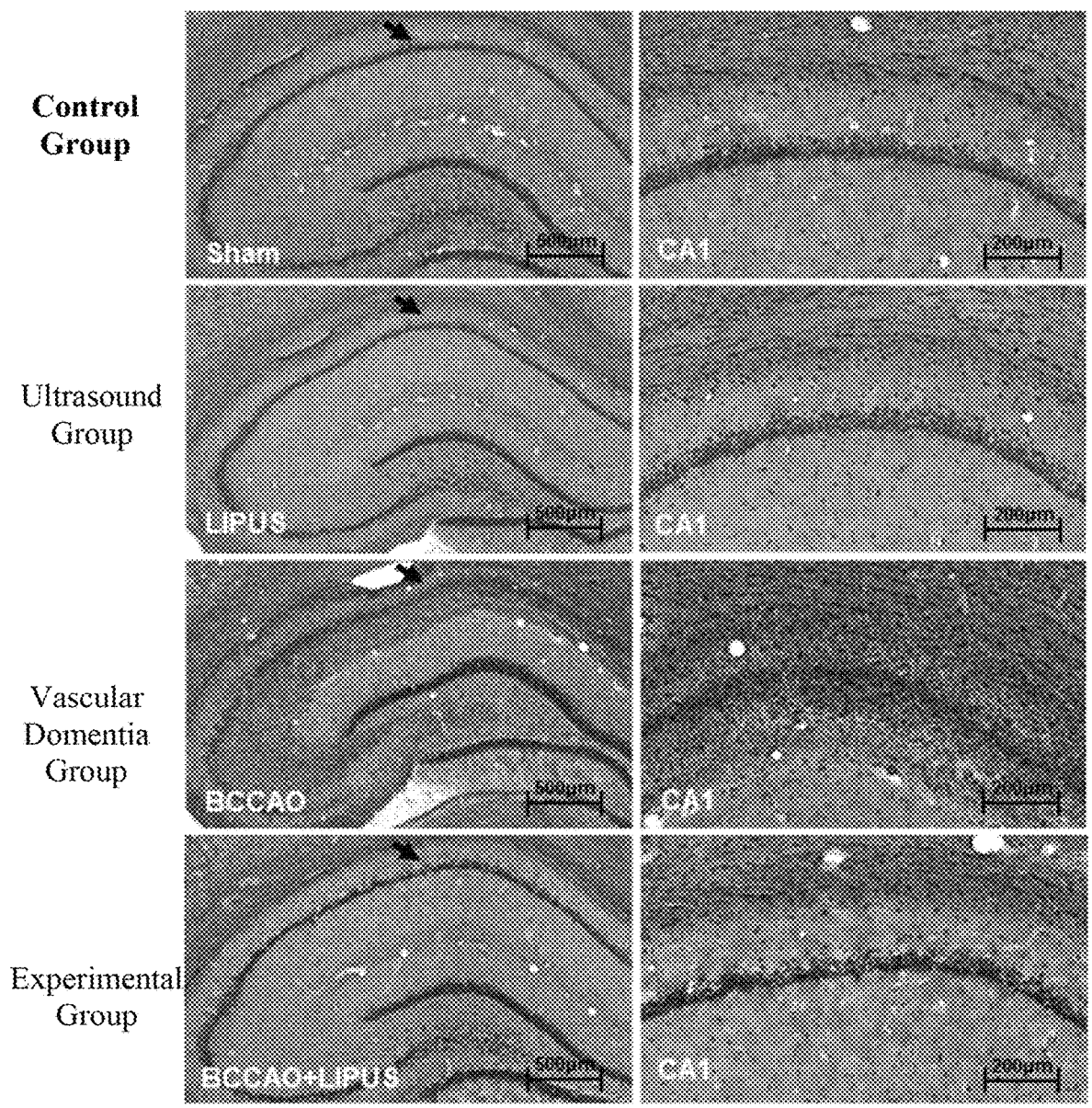
FIG. 10 shows the results of hematoxylin-eosin staining of mice tissue under different conditions.

In addition, hematoxylin and eosin stains of hippocampus of SD rats in the control group, the ultrasound group, the vascular dementia group and the experimental group. The results are shown in FIG. 10, wherein the right column in FIG. 10 is an enlarged view of the hippocampus in the left column. The results showed that the neurons in SD male rat of vascular dementia group were obviously damaged and sparsely distributed. However, in the experimental group, the damaged neurons were significantly recovered after being stimulated with low intensity pulsed ultrasound stimulation for two weeks, and the distribution of neurons was similar to the control group and more concentrated.

Example 6. Effect of Different Days of Ultrasound Stimulation on Protein Expression of Endogenous Neurotrophic Factor The hippocampus of Sprague-Dawley (SD) male rat were treated with low-intensity pulsed ultrasound stimulation with an output frequency of 0.3-1.0 MHz and an output power ($I_{SPTA}$) of 10-720 mW/cm$^2$ for 1, 3, 5 and 7 days (in the experimental group). The time of application was 15 minutes. The SD male rats were sacrificed 7 days later, and Western blotting method was used to observe the expression of BDNF, GDNF and VEGF in brain cells of SD male rat. The results are shown in FIG. 11A, 11B, 11C, wherein the hippocampus of SD male rats in the control group was not applied low-intensity pulsed ultrasound stimulation.

Figure 11A:
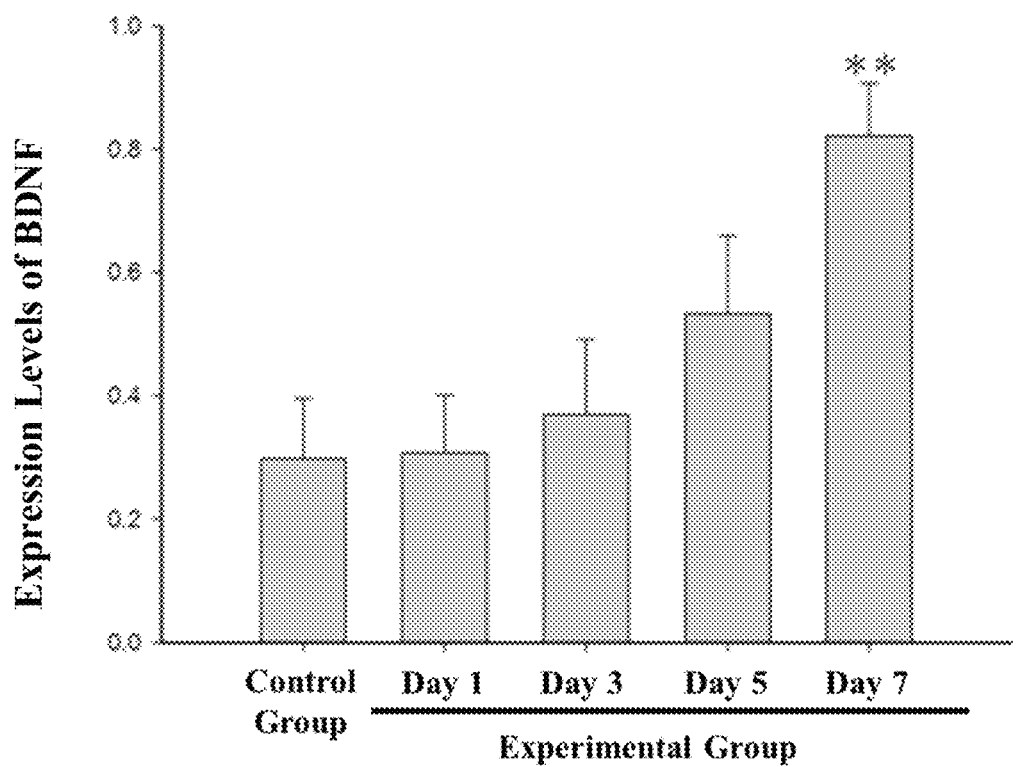
FIG. 11A shows the effect of different days of ultrasound simulation on BDNF expression.
Figure 11B:
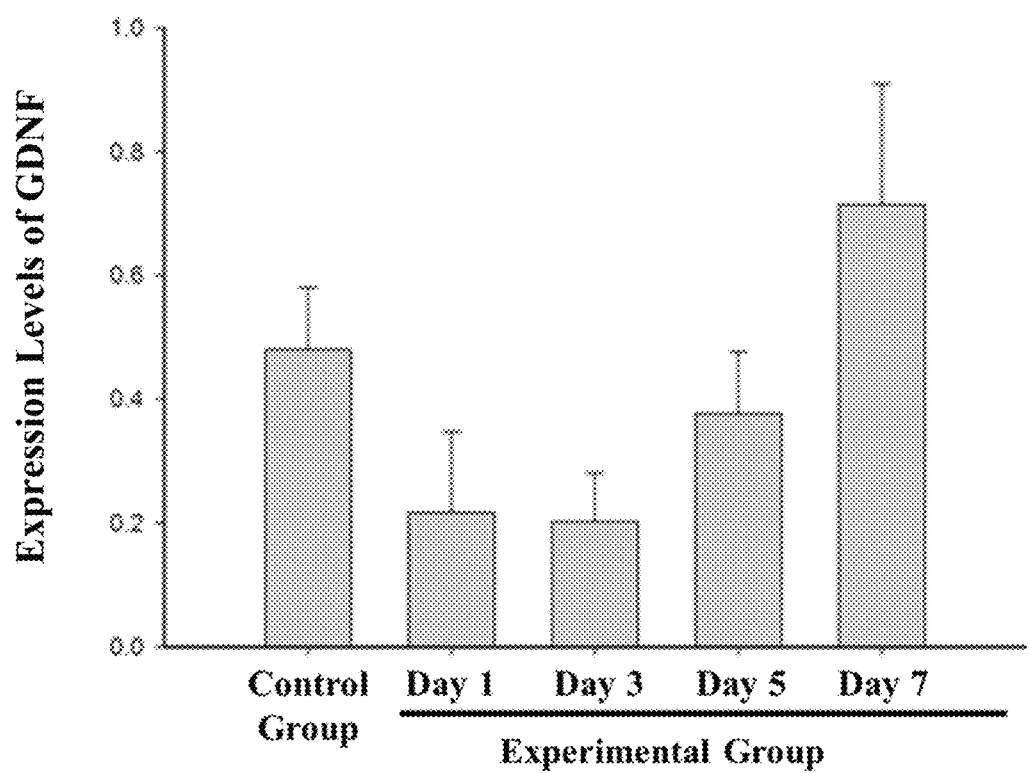
FIG. 11B shows the effect of different days of ultrasound simulation on GDNF expression.
Figure 11C:
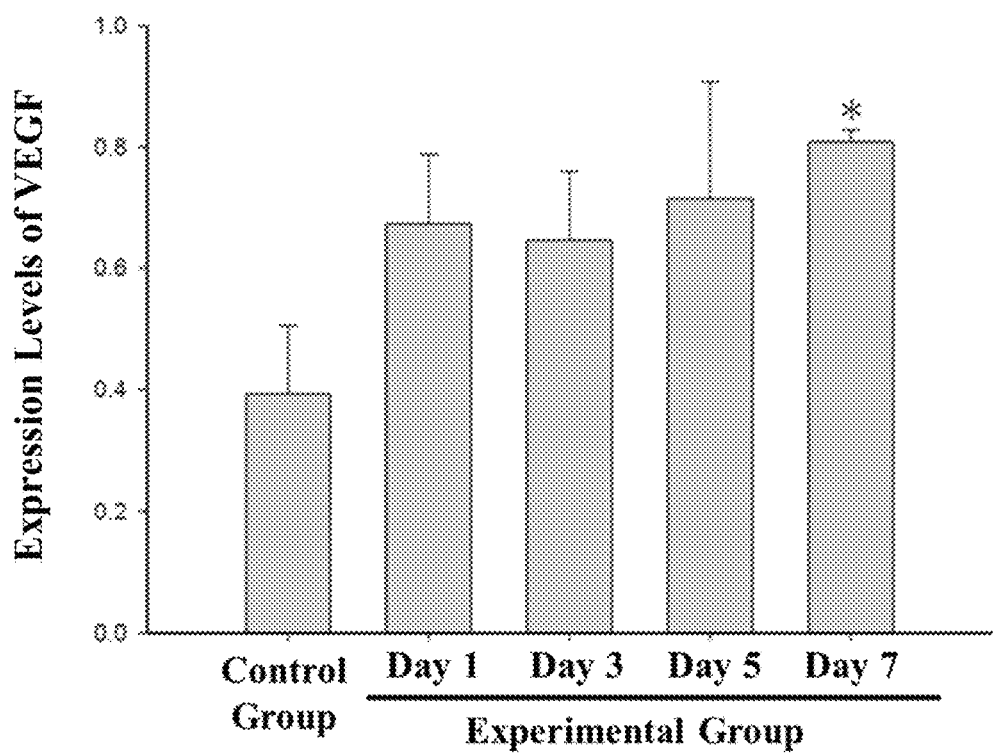
FIG. 11C shows the effect of different days of ultrasound simulation on VEGF expression.

From the above experimental results, compared with the control group, the protein expression of brain neurotrophic factors, including BDNF (as shown in FIG. 11A), GDNF (as shown in FIG. 11B) and VEGF (as shown in FIG. 11C) was significantly increased with the number of days the ultrasound was applied in SD male rats treated with low-intensity pulsed ultrasound stimulation.

In conclusion, the ultrasound stimulation helmet and the method provided by the present invention can be used for regulating the expression of brain endogenous neurotrophic factors and proteins related to neurodegenerative diseases, and therefore have the functions of preventing and treating degenerative brain diseases effect. In addition, the ultrasound stimulation helmet of the present invention is designed with a front adjustment knob and a back adjustment knob, so that it can adapt to different users' head circumference size and is convenient for the user to adjust directly.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. An ultrasound stimulation helmet for regulating the expression of a brain endogenous neurotrophic factor or a neurodegenerative disease-related protein, wherein the ultrasound stimulation helmet comprising:
    a main body, wherein the main body is wearable on a patient's head, the main body comprising a front adjustment knob, a back adjustment knob, a fastening support frame, and a plurality of position adjustment knobs;
    a plurality of ultrasound probes detachably mounted on the main body for generating ultrasound waves, the ultrasound stimulation helmet being characterized in that the ultrasound probes comprise a frequency adjustment knob and an intensity adjustment knob for controlling the output frequency and the output of the ultrasound probe intensity respectively, and other ultrasound parameters and the angle of the ultrasound probe itself are adjustable;
    wherein the fastening support frame adjust the length of the main body according to the size of the head of the patient, and the ultrasound probes are connected with the position adjustment knob of the main body so that the ultrasound probes are moved up, down, left and right according to the patient's head; wherein the ultrasound probes are placed in a position which is positioned relative to the patient's temporal trans-orbital, frontal-temporal cortex, temporal window, sub-mandibular, sub-occipital window; wherein the ultrasound probes comprise a switch for turning on or off the ultrasound probe; wherein the frequency of ultrasound wave is between 20K and 10M Hz; wherein the intensity ($I_{SPTA}$) of ultrasound wave is between 1 mW/cm$^2$ and 10 W/cm$^2$; wherein the parameters of the ultrasound probe of the ultrasound stimulation helmet are adjusted to increase or decrease the expression levels of endogenous neurotrophic factor or neurodegenerative disease-related protein in the brain of the subject.

2. The ultrasound stimulation helmet in claim 1, wherein the feature is the main body comprising a cable fixing portion for fixing the cables of the ultrasound probes.

3. A method for regulating the expression of a brain endogenous neurotrophic factor or a neurodegenerative disease-related protein, comprising:
    (1) Placing the ultrasound stimulation helmet of claim 1 on a subject's head;
    (2) Adjusting the parameters of the ultrasound probe of the ultrasound stimulation helmet to increase or decrease the expression levels of endogenous neurotrophic factor or neurodegenerative disease-related protein in the brain of the subject.

4. The method of claim 3, which the parameter of the adjusted ultrasound probe in the step (2) comprising an output intensity ($I_{SPTA}$), an output frequency or an action time.

5. The method of claim 4, wherein the output intensity is between 1 mW/cm$^2$ and 10 W/cm$^2$.

6. The method of claim 4, wherein the output frequency is between 20K and 10M Hz.

7. The method of claim 4, wherein the action time is between 30 seconds and 60 minutes.

8. The method of claim 3, wherein the brain endogenous neurotrophic factor is selected from one or more of the group consisting of brain-derived neurotrophic factor (BDNF), glial cell-derived neurotrophic factor (GDNF), vascular endothelial growth factor (VEGF) and c-fos protein.

9. The method of claim 3, wherein the neurodegenerative disease-related protein is selected from one or more of the group consisting of TrkB, β-amyloid and acetyl coenzyme A.

* * * * *